United States Patent [19]

Jones et al.

[11] Patent Number: 4,595,013
[45] Date of Patent: Jun. 17, 1986

[54] ELECTRODE HARNESS

[75] Inventors: Randolph W. Jones, Franklin; Alfred S. Callahan, Nashville, both of Tenn.

[73] Assignee: Neurologics, Inc., Nashville, Tenn.

[21] Appl. No.: 642,035

[22] Filed: Aug. 17, 1984

[51] Int. Cl.$^4$ .............................................. A61B 5/04
[52] U.S. Cl. .................................... 128/644; 128/641
[58] Field of Search ............... 128/639, 640, 641, 643, 128/644, 696, 731, 783, 798, 803, 666, 801, 204.23

[56] References Cited

U.S. PATENT DOCUMENTS

| | | | |
|---|---|---|---|
| 3,380,445 | 4/1968 | Frasier | 128/639 |
| 4,029,086 | 6/1977 | Corasanti | 128/641 |
| 4,050,453 | 9/1977 | Castillo et al. | 128/640 |
| 4,067,321 | 1/1978 | Oda et al. | 128/640 |
| 4,082,086 | 4/1978 | Page et al. | 128/640 |
| 4,319,579 | 3/1982 | Cartmell | 128/803 |
| 4,331,153 | 5/1982 | Healy | 128/641 |

OTHER PUBLICATIONS

Blom and Anneveldt, "An Electrode Cap Tested", *Electroencepholography and Clinical Neurophysiology,* 1982, 54:591–594; Electro-Cap Brochure; Electro-Cap International price list.

*Primary Examiner*—Henry J. Recla
*Attorney, Agent, or Firm*—Davis Hoxie Faithfull & Hapgood

[57] ABSTRACT

An electrode harness to be applied to a patient, for use with equipment for monitoring neurological function comprises a flexible adhesive-backed harness pad and a plurality of electrodes mounted on the harness pad such that the contact portions thereof are exposed on the adhesive side of the harness pad at predetermined locations on the pad, to thereby facilitate the accurate and consistent placement of the electrodes on the patient. The electrode harness may also include a pair of earpiece portions having associated electrodes thereon, the earpiece portions being contoured to readily facilitate the application of those portions to the patient's ears in an earring-type manner.

14 Claims, 4 Drawing Figures

ELECTRODE HARNESS

FIELD OF THE INVENTION

The present invention is directed to the field of physiological monitoring devices and in particular, the field of electroencephalographic (EEG) monitoring.

BACKGROUND OF THE INVENTION

EEG monitoring is a well known technique for determining brain function. The importance of continuous EEG monitoring during specific high-risk cerebrovascular processes is becoming widely acknowledged. It is recognized that EEG frequency and amplitude changes precede the development of neurological dysfunction and early therapeutic intervention can reverse this change or prevent further deterioration.

Heretofore, the monitoring of EEG signals with prior art EEG monitors has been an extremely cumbersome task requiring the use of large, bulky polygraphs and skilled technicians in order to interpret the EEG signals. The EEG signals are of a highly complex nature, involving a variety of signals such as alpha waves and beta waves, which are low in amplitude and vary rapidly with time. Rapid interpretation of the signals has therefore been extremely difficult, and appreciable time and operator experience is required for interpretation of this type of EEG output.

Some of the problems associated with the intraoperative utility of EEG monitoring, such as signal interpretation and bulky equipment, have been eliminated by a new generation of compact devices which display processed EEG data. Specifically, the PSA-1 ™ EEG monitor, described in U.S Pat. Nos. 4,412,547 and 4,424,816, and produced by Neurologics, Inc., assignee of the present invention, provides precise measurement of a patient's electrocerebral activity, without the need for large, bulky polygraphs and skilled technicians. The PSA-1 ™ EEG monitor provides easy to read displays for early detection of changes in brain function due to ischemia or hypotension, and the monitor's solid state circuitry provides reliable, instantaneous assessment of unit function and calibration.

As with other physiological monitoring systems, the reliability, precision and accuracy of an EEG monitoring system relies, at least in part, upon the precise and accurate placement of the electrodes on predetermined areas of the patient's head. For example, classical EEG procedure has, for many years, called for the placement of "reference" electrodes on the earlobes of a patient. Using the PSA-1 ™ EEG monitor, it is suggested that three electrodes be equally spaced laterally across the patient's forehead, in addition to the reference electrodes applied to the patient's earlobes. Typically, the electrodes are provided in the form of either needle electrodes or "stick-on" electrodes, and are applied individually to the predetermined areas of the patient's head.

This method of placement of the electrodes on the patient is many times a limiting factor in the reliability, accuracy and precision of the output of the EEG monitor. When variations in the absolute or relative locations of the electrodes occur, as for example when the two outer electrodes applied to the patient's forehead are misplaced with respect to the middle electrode, imprecise, inaccurate and/or unreliable results may be produced.

Furthermore, problems can arise if any of the five electrodes becomes dislodged or otherwise fails to maintain proper contact with the patient's skin. This problem is particularly acute when attaching the reference electrodes to the patient's earlobes, due to the irregular surface thereof. Because of the difficulties in firmly attaching an electrode to the earlobe, many EEG technicans instead attach the electrode over the mastoid region, behind the ear. The difficulty with using the mastoid region is that it is often contaminated by muscle artifact. Although muscle artifact is sometimes less a consideration in the operating room because of the use of muscular paralyzing agents, it is nevertheless advisable to reduce such artifact whenever possible. Further, in some patients the mastoid region can be an active electrical site, so that the EEG which is detected is not the same as would be obtained using the electrically neutral site of the earlobe.

OBJECTS AND SUMMARY OF THE INVENTION

It is an object of the present invention to overcome the difficulties associated with the prior art techniques of applying electrodes to patients for the purpose of neurological monitoring.

It is a further object of the present invention to provide an electrode harness which readily allows the precise, secure and accurate location and placement of electrodes on a patient.

It is a further object of the invention to provide a convenient technique for storing and transporting an electrode harness prior to use.

Briefly, an electrode harness to be applied to a patient, for use with equipment for monitoring neurological function, comprises a flexible adhesive-backed forehead pad having an adhesive on one side thereof, and a plurality of forehead electrodes having respective contact portions, each of the forehead electrodes being mounted on the forehead pad such that the contact portions thereof are exposed on the adhesive side of the forehead pad at predetermined locations on the pad, to thereby facilitate the accurate and consistent placement of the electrodes on the patient when the adhesive side of the forehead pad is applied to the patient.

Preferably, the forehead pad is in the form of a flexible strip of material, and the electrodes are colinearly provided along the strip. Three electrodes are preferably provided on the strip, the middle electrode being approximately midway between the outer two electrodes.

A pair of earpiece portions, are also provided as part of the electrode harness. Each earpiece portion comprises a flexible adhesive-backed earpiece pad having an adhesive on one side thereof, and an electrode having a contact portion, mounted on the earpiece pad such that the contact portion thereof is exposed on the adhesive side thereof. The earpiece pad is preferably contoured to readily facilitate the application of the earpiece pad and associated electrode to the earlobe of the patient in an earring type manner. The electrode harness is preferably mounted on a base contoured to hold the electrode harness prior to use. The adhesive-backed forehead and earpiece pads are temporarily and adhesively secured to the base such that the pads may be peeled off from the base for application to a patient.

The base preferably contains a plurality of reservoirs of conductive gel at locations corresponding to the locations of the electrodes when the adhesive pads are secured to the base.

BRIEF DESCRIPTION OF THE DRAWINGS

These and other objects and aspects of the invention will be more fully described with reference to the following drawing figures.

DETAILED DESCRIPTION OF THE INVENTION

Figure 1:
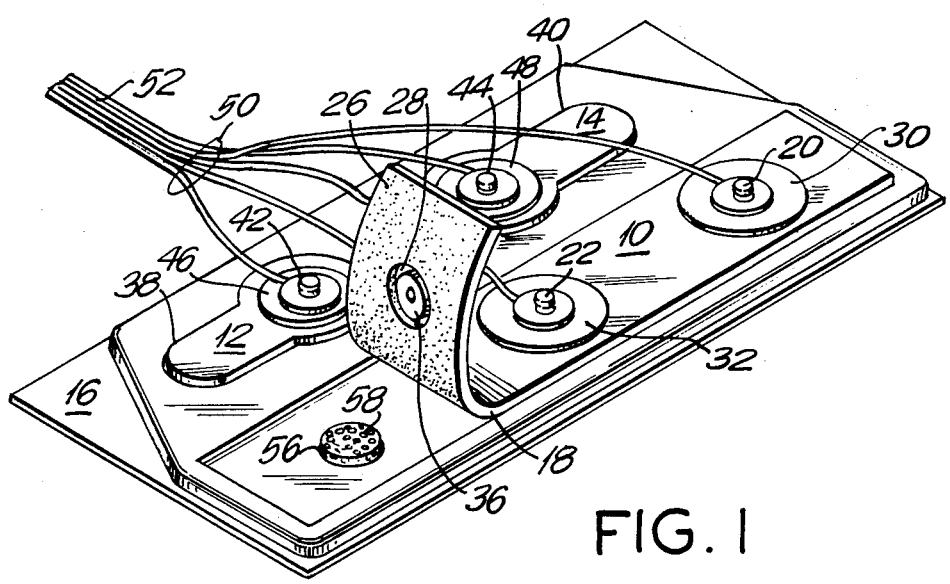
FIG. 1 is a perspective view of the electrode harness in accordance with the present invention mounted upon a base contoured to hold the harness prior to use.

With reference to FIG. 1, the electrode harness in accordance with the present invention is comprised of three separate sections, namely forehead pad 10, and earpiece portions 12 and 14. The electrode harness is shown mounted on base 16, which is contoured to hold the forehead pad 10 and earpiece portions 12 and 14 prior to use. The forehead pad 10 is comprised of a flexible, adhesive-backed foam strip 18 having three electrodes 20, 22 and 24 colinearly mounted thereon. The flexible strip of material 18, having an adhesive 26 on the back thereof, is provided with three apertures (only one of which, 28, is shown), through which the electrodes 20, 22 and 24 extend.

Figure 3:
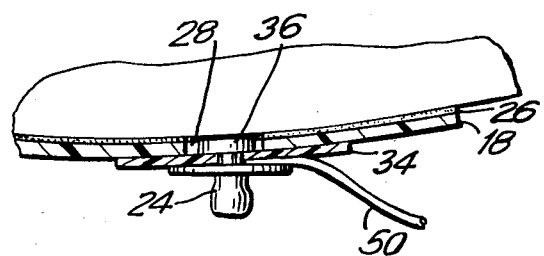
FIG. 3 is a cross sectional view taken through section 3—3 in FIG. 2.

With further reference to FIG. 3, the electrodes 20, 22 and 24 are mounted on strip 18 by means of respective connector pieces 30, 32 and 34, such that the contact portions of the electrodes, (one of which, 36, is shown), are exposed on the adhesive side of the flexible strip 18. The connector pieces are secured, on one hand, around the periphery of their respective electrodes and are secured, on the other hand, to the strip 18 about the circumference of their respective apertures.

Earpiece portions 12 and 14 are similarly comprised of flexible adhesive-backed foam strips 38 and 40 and associated electrodes 42 and 44, mounted, through associated apertures in the strips 38 and 40, by means of respective connector pieces 46 and 48, so as to provide the contacts of the electrodes 42 and 44 on the adhesive side of the strips 38 and 40, in a manner substantially identical to that shown for electrodes 20, 22 and 24.

Connected to each of the five electrodes is an associated one of a plurality of wires 50 which are eventually joined into a single ribbon-type cable 52, for application to an EEG monitoring device 54 (FIG. 2), by means of a suitable connector. The wires 50 are preferably color-coded to help identify to which of the electrodes a particular wire is connected.

The base 16 is contoured to conveniently store the electrode harness prior to use, and is provided with a smooth surface for backing the strips 18, 38 and 40, so that the strips can easily be pealed off the base for application to a patient. The base 16 preferably includes a plurality of reservoirs, one of which, 56, is shown in FIG. 1, underneath each of the electrodes 20, 22, 24, 42 and 44 such that the contact portions of the electrodes are presupplied with a commonly used conductive gel. The harness may therefore be taken off base 16 and applied directly to the patient without any intermediate steps. The reservoirs may include a piece of porous foam 58, or the like, in order to stabilize the gel within the reservoir.

Figure 2:
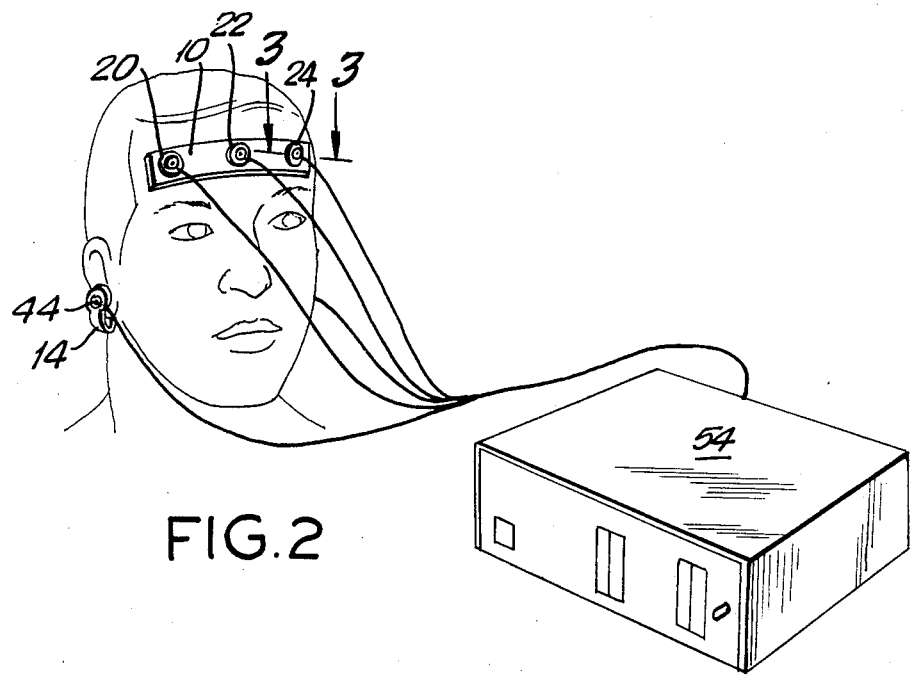
FIG. 2 is an illustration of the electrode harness of FIG. 1, applied to a patient for EEG monitoring.

FIG. 2 illustrates the use of the electrode harness for EEG applications. The forehead pad 10 is placed on the patient's forehead so as to dispose the electrodes 20, 22 and 24 laterally across the patient's forehead. Normally, the middle electrode 22 will be placed in the middle of the harness pad 10, and electrodes 20 and 24 an equal distance on either side of the electrode 22, to thereby provide a bilaterally symmetrical placement of the electrodes across the patient's forehead. Thus, the use of the forehead pad 10 readily facilitates the accurate and precise placement of the electrodes on a patient, and further provides for the constant and secure contact of the electrodes to the patient by means of the preloaded conductive gel and the wide surface area provided by the forehead pad 10.

The earpiece portions 12 and 14 are placed on the patient's earlobe in an "earring-type" manner thereby also providing a firm and secure contact of the associated electrodes 42 and 44 at precise locations. Further, the earring-type structure helps insure that the electrodes will not become dislodged from the earlobes, thereby eliminating the possibility of improper readings during surgery.

Figure 4:
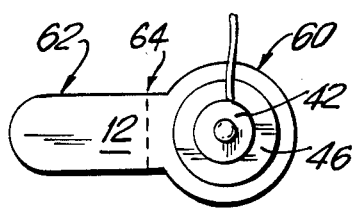
FIG. 4 is a plan view of the earpiece portion of the electrode harness illustrated in FIG. 1.

FIG. 4 illustrates a plan view of the earpiece portion 12. As shown in the figure, the earpiece portion includes a generally circular main portion 60 upon which the electrode 42 is mounted, and an appendage portion 62 connected to the circular portion 60. As shown in FIG. 2, the earpiece portion is adapted to flex between the circular portion 60 and the appendage 62, at flexing region 64, when applied to the patient's ear. The earpiece portion shown in FIG. 4 has a generally straight appendage, although other configurations will become apparent to those skilled in the art.

The flexible strips 18, 38 and 40 may be made of a soft styrofoam material, the connector pieces 30,32,34, 46 and 48, may be made of a flexible material such as vinyl, and the base 16 may be a lightweight plastic such as polystyrene or polyvinyl chloride. However, many alternative materials may be employed, as will be appreciated by those skilled in the art.

Other changes and variations to the present invention will occur to those skilled in the art in view of the foregoing description. It is intended that such changes and variations be encompassed so long as the present invention is employed, as defined by the following claims.

What is claimed is:

1. A process for applying an electrode to a patient undergoing neurological monitoring, comprising the steps of adhering a main, electrode-bearing portion of a flexible, adhesive-backed earpiece pad to a first side of an earlobe of said patient, said electrode-bearing portion sized to fit substantially over only said earlobe whereby said electrode in said main portion is in contact with said first side of said patient's earlobe;

bending a flexible appendage portion of said earpiece pad, connected to and extending substantially radially from said main portion, around the patient's earlobe; and adhering at least an end of said appendage portion to the other side of said patient's earlobe opposite to said first side.

2. The process of claim 1 wherein said step of bending consists essentially of the step of bending a single appendage around the patient's earlobe.

3. The process of claim 2 wherein said step of applying a main portion includes applying a substantially circular main portion, and said step of bending includes bending a substantially straight appendage portion.

4. The process of claim 1 further including the step of removing said adhesive-backed earpiece pad from a contoured base.

5. The process of claim 1 further comprising the step of
applying a flexible, adhesive-backed, electrode-bearing forehead pad to the forehead of said patient, such that at least one electrode on said forehead pad is in contact with said patient's forehead.

6. The process of claim 5 wherein said step of applying said forehead pad includes applying a forehead pad having three co-linearly mounted electrodes thereon.

7. An electrode earpiece for application to the earlobe of a patient, for use with equipment for monitoring neurological function, comprising:
an electrode having a contact and a wire electrically connected to said contact; and
a flexible, adhesive-backed earpiece pad having (i) a main portion sized to fit substantially over only an earlobe of a patient, said electrode being mounted thereon such that said contact is exposed on the adhesive side of said earpiece pad, (ii) an appendage connected to and extending substantially radially from said main portion, and (iii) a flexing region proximate to the intersection of said main portion and said appendage, to thus facilitate the adhesion of said main portion with said electrode, to a first side of said patient's earlobe, and the adhesion of said appendage to the opposite side of said patient's earlobe.

8. The electrode earpiece of claim 7 wherein said main portion is substantially circular, and said earpiece pad includes a single, substantially straight appendage.

9. The electrode earpiece of claim 7 in further combination with a flexible, adhesive-backed forehead pad having a plurality of forehead electrodes mounted thereon such that said forehead electrodes are in contact with the forehead of said patient when said forehead pad is applied to said patient's forehead.

10. The combination electrode earpiece and forehead pad of claim 9, wherein three forehead electrodes are co-linearly mounted on said forehead pad.

11. An electrode earpiece for application to the earlobe of a patient, for use with equipment for monitoring neurological function, comprising:
an electrode having a contact and a wire electrically connected to said contact;
an adhesive-backed, main earpiece pad means for adhering to a first side of a patient's earlobe, said main earpiece pad means sized to fit substantially over only a patient's earlobe, said electrode being mounted thereon such that said contact is applied to said first side of the patient's earlobe; and
a single, flexible, adhesive-backed appendage means, connected to and extending substantially radially from said main earpiece pad means, for bending around the patient's earlobe, from said first side to the other side of said patient's earlobe to be adhered thereto to facilitate the adhesion of said electrode to said patient's earlobe.

12. The electrode earpiece of claim 11 wherein said main earpiece pad means is substantially circular, and said appendage means is substantially straight.

13. The electrode earpiece of claim 11, in further combination with a flexible, adhesive-backed forehead pad means for carrying a plurality of forehead electrodes thereon, and for application to a patient's forehead such that said forehead electrodes are in contact with the forehead of said patient.

14. The combination electrode earpiece and forehead pad means of claim 13, wherein three forehead electrodes are co-linearly mounted on said forehead pad.

* * * * *